United States Patent
Li et al.

(10) Patent No.: US 11,701,191 B1
(45) Date of Patent: Jul. 18, 2023

(54) INTERVENTIONAL ROBOT SYSTEM, AND CONTROL METHOD AND READABLE-STORAGE MEDIUM THEREOF

(71) Applicant: SHENZHEN INSTITUTE OF ADVANCED BIOMEDICAL ROBOT CO., LTD., Shenzhen (CN)

(72) Inventors: Zhenglong Li, Shenzhen (CN); Jun Huang, Shenzhen (CN); Gang Yao, Shenzhen (CN)

(73) Assignee: SHENZHEN INSTITUTE OF ADVANCED BIOMEDICAL ROBOT CO., LTD., Shenzhen (CN)

( * ) Notice: Subject to any disclaimer, the term of this patent is extended or adjusted under 35 U.S.C. 154(b) by 0 days.

(21) Appl. No.: 18/091,422

(22) Filed: Dec. 30, 2022

Related U.S. Application Data (63) Continuation of application No. PCT/CN2022/115870, filed on Aug. 30, 2022.

(30) Foreign Application Priority Data

Apr. 24, 2022 (CN) .......................... 202210432678.1

(51) Int. Cl.
*A61B 34/20* (2016.01)
*A61B 34/37* (2016.01)
*A61B 90/00* (2016.01)

(52) U.S. Cl.
CPC .............. *A61B 34/37* (2016.02); *A61B 90/06* (2016.02)

(58) Field of Classification Search
CPC .......... F28D 15/02; F28F 1/14; A61B 90/361; A61B 34/72; A61B 1/00087; A61B 34/71;
(Continued)

(56) References Cited

U.S. PATENT DOCUMENTS 8,190,238 B2 * 5/2012 Moll ...................... A61B 34/71
715/702
9,333,042 B2 * 5/2016 Diolaiti .................. A61B 34/72
(Continued)

FOREIGN PATENT DOCUMENTS

CN 108582082 A 9/2018
CN 108858189 A 11/2018
(Continued)

OTHER PUBLICATIONS

Rosati et al., First experimental results of an integrated robotic system for haptic teleoperation, 2007, IEEE, p. 3138-3143 (Year: 2007).*

(Continued)

*Primary Examiner* — McDieunel Marc (57) ABSTRACT

An interventional robot system and a readable storage medium. In the interventional robot system, a touch switch is arranged on an operation lever and connected to a processor, and is configured to send a current switch state to the processor; a master-end encoder is arranged on the operation lever and connected to the processor, and is configured to send to the processor an operation lever displacement generated in response to the operation lever being controlled to perform a current operation; a null sensor is arranged on a base and connected to the processor, and is configured to send a current sensor state to the processor; and the processor is configured to control an interventional robot slave end to perform a movement corresponding to the operation lever displacement, such that an elongated medical instrument is accurately controlled to move, and invalid operations are eliminated.

10 Claims, 4 Drawing Sheets

(58) Field of Classification Search
CPC ......... A61B 34/30; A61B 90/37; A61B 34/37; A61B 1/00193; A61B 2034/305; A61B 2034/2061; A61B 1/018; A61B 2017/00278; A61B 2017/00694; A61B 34/20; A61B 1/0055; A61B 2017/3447; A61B 2034/306; A61B 2034/301
See application file for complete search history.

(56) References Cited

U.S. PATENT DOCUMENTS

| | | | |
|---|---|---|---|
| 9,539,058 B2* | 1/2017 | Tsekos | F16C 1/20 |
| 11,311,342 B2* | 4/2022 | Parihar | A61B 34/37 |
| 2007/0197896 A1* | 8/2007 | Moll | A61B 50/13 600/407 |
| 2014/0058406 A1* | 2/2014 | Tsekos | A61B 34/30 606/130 |

FOREIGN PATENT DOCUMENTS

| | | |
|---|---|---|
| CN | 110772325 A | 2/2020 |
| CN | 110879632 A | 3/2020 |
| CN | 111065351 A | 4/2020 |
| CN | 111494014 A | 8/2020 |
| CN | 113384352 A | 9/2021 |
| CN | 113749779 A | 12/2021 |
| CN | 113995513 A | 2/2022 |
| CN | 215874929 U | 2/2022 |
| CN | 114521971 A | 5/2022 |
| JP | 2012071406 A | 4/2012 |
| WO | 2015014668 A1 | 2/2015 |

OTHER PUBLICATIONS

Qingcheng et al., Research and implementation of master-slave control for interventional robot system, 2017, IEEE, p. 234-239 (Year: 2017).*
Gupta et al., Master-Slave Control of a Teleoperated Anthropomorphic Robotic Arm With Gripping Force Sensing, 2006, IEEE, p. 2136-2145 (Year: 2006).*
Guo et al., A Novel Master-slave Robotic System with Close Loop Control for Vascular Interventional Surgery, 2018, IEEE, p. 591-596 (Year: 2018).*
International Search Report issued in corresponding International application No. PCT/CN2022/115870, mailed Nov. 24, 2022.
Written Opinion of the International Search Authority in corresponding International application No. PCT/CN2022/115870.

* cited by examiner

FIG. 7

INTERVENTIONAL ROBOT SYSTEM, AND CONTROL METHOD AND READABLE-STORAGE MEDIUM THEREOF

CROSS REFERENCE TO RELATED APPLICATIONS

This application a continuation application of International Application No. PCT/CN2022/115870 filed on Aug. 30, 2022, which claims priority to Chinese Patent Application No. 202210432678.1, filed on Apr. 24, 2022 and entitled "INTERVENTIONAL ROBOT SYSTEM, AND CONTROL METHOD AND READABLE-STORAGE MEDIUM THEREOF," the disclosure of which is incorporated herein by reference in its entirety.

TECHNICAL FIELD

The present disclosure relates to the technical field of medical robots, and in particular, relates to an interventional robot system, and a control method and a readable-storage medium thereof.

BACKGROUND

An interventional robot includes a master-end control apparatus and an interventional robot slave end connected to the master-end control apparatus. An operator operates on the master-end control apparatus, and sends operation information to the interventional robot slave end, to allow the interventional robot slave end to perform a corresponding operation. However, during use, it is found that the master-end control apparatus may be subject to a plurality of types of invalid operations that are not easily noticed by the operator. As a result, the operation of the interventional robot slave end may be subject to errors, and the expectation of the operator fails to be fulfilled.

SUMMARY

Technical Problem

The master-end control apparatus of the interventional robot may be subject to invalid operations, and consequently the operation of the interventional robot slave end is subject to errors.

Technical Solution

Various embodiments of the present disclosure provide an interventional robot system, and a control method and a readable-storage medium thereof to overcome the drawbacks in the related art.

According to one aspect of the embodiments of the present disclosure, an interventional robot system is provided. The interventional robot system includes a processor, a master-end control apparatus, and an interventional robot slave end, wherein the master-end control apparatus includes a base, an operation lever, a touch switch, a master-end encoder, and a null sensor; wherein the touch switch is arranged on the operation lever and connected to the processor, and is configured to send a current switch state to the processor;

the master-end encoder is arranged on the operation lever and connected to the processor, and is configured to send to the processor an operation lever displacement generated in response to the operation lever being controlled to perform a current operation;

the null sensor is arranged on the base and connected to the processor, and is configured to send a current sensor state to the processor; and the processor is configured to: acquire the operation lever displacement sent by the master-end encoder, the current sensor state sent by the null sensor, and the current switch state sent by the touch switch; determine, based on the current sensor state and the current switch state, whether the current operation is valid; in response to determining that the current operation is valid, acquire target control information based on the operation lever displacement and send the target control information to the interventional robot slave end, such that the interventional robot slave end controls an elongated medical instrument to move based on the target control information; and in response to determining that the current operation is invalid, acquire a processing result by processing the operation lever displacement based on the current sensor state and the current switch state.

In some embodiments, the null sensor is arranged on the base, and is disposed between a head end of the operation lever and a tail end of the operation lever.

The embodiments of the present disclosure further provide a readable storage medium. The readable storage medium stores one or more computer programs, wherein the one or more computer programs, when loaded and run by a processor, cause the processor to perform a method for controlling an interventional robot including:

(1) acquiring current parameters, the current parameters including an operation lever displacement sent by a master-end encoder, a current sensor state sent by a null sensor, and a current switch state sent by a touch switch, wherein the operation lever displacement is a displacement generated in response to the operation lever being controlled to perform a current operation;

(2) determining, based on the current sensor state and the current switch state, whether the current operation is valid;

(3) in response to determining that the current operation is valid, acquiring target control information based on the operation lever displacement and sending the target control information to an interventional robot slave end, such that the interventional robot slave end controls an elongated medical instrument to move based on the target control information;

(4) in response to determining that the current operation is invalid, acquiring a processing result by processing the operation lever displacement based on the current sensor state and the current switch state.

In some embodiments, step (2) includes:

determining that the current operation is invalid in the case that the current sensor state is ENABLED;

determining whether the current switch state is DISABLED in the case that the current sensor state is DISABLED;

determining that the current operation is invalid in the case that the current switch state is DISABLED; and determining that the current operation is valid in the case that the current switch state is ENABLED.

In some embodiments, in the case that the current sensor state is ENABLED and the current operation is invalid, acquiring the processing result by processing the operation lever displacement based on the current sensor state and the current switch state includes:

determining the operation lever displacement corresponding to the current operation as 0 in the case that the current switch state is ENABLED.

In some embodiments, the master-end control apparatus further includes a motor connected to the processor; and in the case that the current sensor state is DISABLED, the current switch state is DISABLED, and the current operation is invalid, acquiring the processing result by processing the operation lever displacement based on the current sensor state and the current switch state includes:

sending a motor start signal to the motor, such that the motor controls the operation lever to perform a reset operation and resets the operation lever displacement.

In some embodiments, in the case that the current sensor state is DISABLED, the current switch state is ENABLED, and the current operation is valid, acquiring the target control information based on the operation lever displacement includes:

determining whether a displacement absolute value corresponding to the operation lever displacement is not greater than a standard value;

in response to determining that the displacement absolute value is greater than the standard value, acquiring an ultimate displacement, determining the ultimate displacement as a target displacement, and acquiring the target control information based on the target displacement; or in response to determining that the displacement absolute value is not greater than the standard value, determining the operation lever displacement as a target displacement, and acquiring the target control information based on the target displacement.

In some embodiments, acquiring the target control information based on the target displacement includes:

acquiring a displacement-speed mapping relationship by querying a database; and acquiring, based on the displacement-speed mapping relationship, a target speed corresponding to the target displacement, and determining the target speed as the target control information.

In some embodiments, acquiring the target control information based on the target displacement includes:

acquiring adjacent history displacements, and a target increment displacement based on the target displacement and the adjacent history displacements; and determining the target increment displacement as the target control information.

In some embodiments, the master-end control apparatus further includes an instrument change switch connected to the processor, and the current parameters further include a target drive identifier sent by the instrument change switch; and in step (3), the target drive identifier and the target control information are sent to the interventional robot slave end, such that the interventional robot slave end controls the elongated medical instrument corresponding to the target drive identifier to move based on the target control information.

According to another aspect of the embodiments of the present disclosure, a method for controlling an interventional robot is provided, which is applicable to the interventional robot system as described above. The method includes:

acquiring current parameters, the current parameters including an operation lever displacement sent by a master-end encoder, a current sensor state sent by a null sensor, and a current switch state sent by a touch switch, wherein the operation lever displacement is a displacement generated in response to the operation lever being controlled to perform a current operation;

determining, based on the current sensor state and the current switch state, whether the current operation is valid;

in response to determining that the current operation is valid, acquiring target control information based on the operation lever displacement and sending the target control information to an interventional robot slave end, such that the interventional robot slave end controls an elongated medical instrument to move based on the target control information;

in response to determining that the current operation is invalid, acquiring a processing result by processing the operation lever displacement based on the current sensor state and the current switch state.

In some embodiments, determining, based on the current sensor state and the current switch state, whether the current operation is valid includes:

determining that the current operation is invalid in the case that the current sensor state is ENABLED;

determining whether the current switch state is DISABLED in the case that the current sensor state is DISABLED;

determining that the current operation is invalid in the case that the current switch state is DISABLED; and determining that the current operation is valid in the case that the current switch state is ENABLED.

In some embodiments, in the case that the current sensor state is ENABLED and the current operation is invalid, acquiring the processing result by processing the operation lever displacement based on the current sensor state and the current switch state includes:

determining the operation lever displacement corresponding to the current operation as 0 in the case that the current switch state is ENABLED.

In some embodiments, the master-end control apparatus of the interventional robot system further includes a motor connected to the processor; and in the case that the current sensor state is DISABLED, the current switch state is DISABLED, and the current operation is invalid, acquiring the processing result by processing the operation lever displacement based on the current sensor state and the current switch state includes:

sending a motor start signal to the motor, such that the motor controls the operation lever to perform a reset operation and resets the operation lever displacement.

In some embodiments, in the case that the current sensor state is DISABLED, the current switch state is ENABLED, and the current operation is valid, acquiring the target control information based on the operation lever displacement includes:

determining whether a displacement absolute value corresponding to the operation lever displacement is not greater than a standard value;

in response to determining that the displacement absolute value is greater than the standard value, acquiring an ultimate displacement, determining the ultimate displacement as a target displacement, and acquiring the target control information based on the target displacement; or in response to determining that the displacement absolute value is not greater than the standard value, determining the operation lever displacement as a target displacement, and acquiring the target control information based on the target displacement.

In some embodiments, acquiring the target control information based on the target displacement includes:

acquiring a displacement-speed mapping relationship by querying a database; and acquiring, based on the displacement-speed mapping relationship, a target speed corresponding to the target displacement, and determining the target speed as the target control information.

In some embodiments, acquiring the target control information based on the target displacement includes:

acquiring adjacent history displacements, and a target increment displacement based on the target displacement and the adjacent history displacements; and determining the target increment displacement as the target control information.

In some embodiments, the master-end control apparatus of the interventional robot system further includes an instrument change switch connected to the processor, and the current parameters further include a target drive identifier sent by the instrument change switch;

while sending the target control information to the interventional robot slave end, the method further includes: sending the target drive identifier to the interventional robot slave end; and controlling, by the interventional robot slave end, the elongated medical instrument to move based on the target control information includes: causing the interventional robot slave end to control the elongated medical instrument corresponding to the target drive identifier to move based on the target control information.

Beneficial Effects

In summary, the embodiments of the present disclosure provide an interventional robot system, and a control method and a readable storage medium thereof. The processor determines, based on the current sensor state and the current switch state, whether the current operation of the operation lever on the lever core is valid, and controls the elongated medical instrument to perform the corresponding operation only in the case that the current operation is valid, such that the control accuracy is ensured. In the case that the current operation of the operation lever on the lever core is valid, the target control information is acquired based on the operation lever displacement, and the target driver identifier and the target control information are sent to the interventional robot slave end, such that the interventional robot slave end controls the elongated medical instrument corresponding to the target drive identifier to move based on the target control information. In this way, the elongated medical instrument is flexibly controlled to move, and operation needs of different operators and the needs of different operation speeds are accommodated. In the case that the current operation of the operation lever on the lever core is invalid, the operation lever displacement is processed based on the current sensor state and the current switch state to acquire the processing result. In this way, the invalid operation is canceled, the surgical effect desired by the operator is achieved, and the interventional surgery is ensured successful.

Reference numerals and denotations thereof:

10—base; 11—first bearing seat; 12—second bearing seat; 13—lever core; 14—operation lever; 15—touch switch; 16—master-end encoder; and 17—null sensor.

DETAILED DESCRIPTION

For clearer descriptions of the objects, technical solutions, and advantages of the present disclosure, the present disclosure is further described with reference to specific embodiments and attached drawings. It should be understood that the specific embodiments described herein are only intended to explain the present disclosure instead of limiting the present disclosure.

Embodiments of the present disclosure provide an interventional robot system. The interventional robot system includes a processor, and a master-end control apparatus and an interventional robot slave end that are communicably connected to the processor.

Figure 1:
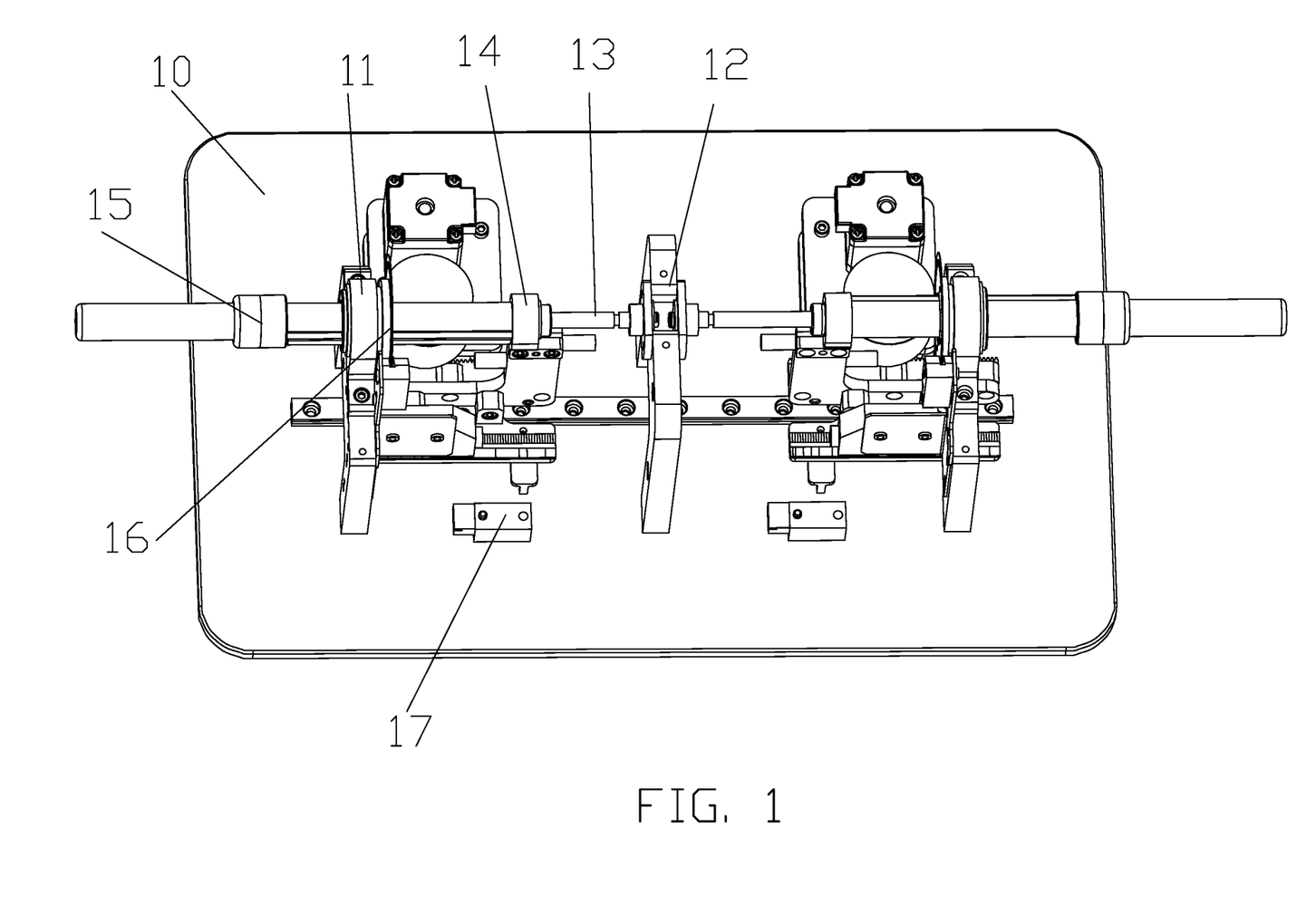
FIG. 1 is a schematic structural diagram of an interventional robot system according to some embodiments of the present disclosure.
Figure 2:
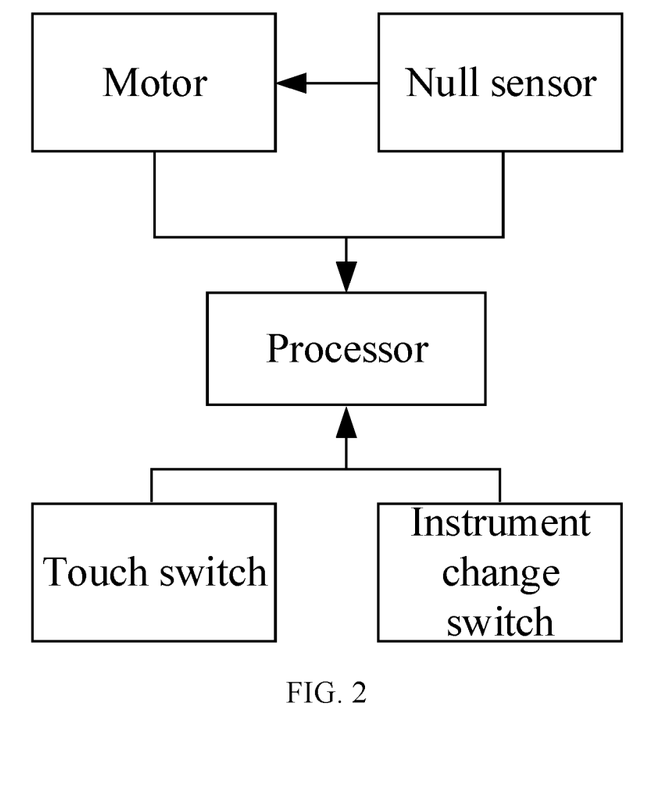
FIG. 2 is a schematic diagram of device interaction in the interventional robot system according to some embodiments of the present disclosure.

As illustrated in FIG. 1 and FIG. 2, the master-end control apparatus includes a base 10, a first bearing seat 11 and a second bearing seat 12 that are mounted on the base 10, a lever core 13 inserted into the first bearing seat 11 and the second bearing seat 12, an operation lever 14 slidably arranged on the lever core 13, a touch switch 15 mounted on the operation lever 14, a master-end encoder 16 connected to the operation lever 14, and a null sensor 17 disposed between a head end and a tail end of the lever core 13. The null sensor 17 is disposed between the first bearing seat 11 and the second bearing seat 12. The operation lever 14 is capable of displacing (including rotary movement and axial movement) along an axis center on the lever core 13. The processor is communicably connected to the touch switch 15, the master-end encoder 16, and the null sensor 17. In the present disclosure, in the case that an operator controls the operation lever 14 to move forward or move backward on the lever core 13, the master-end encoder 16 records an operation lever displacement of the operation lever 14, and sends the operation lever displacement to the processor at intervals of a predetermined duration. The processor is equipped with a computer program to perform related steps to acquire target control information corresponding to the operation lever displacement generated by the operation lever 14 under a valid operation. In this way, the interventional robot slave end is accurately controlled based on the target control information, and errors are prevented. The predetermined duration is a predefined time length.

An embodiment of the present disclosure provides an interventional robot system. The interventional robot system includes a processor, and a master-end control apparatus and an interventional robot slave end that are communicably connected to the processor.

As illustrated in FIG. 1 and FIG. 2, the master-end control apparatus includes a base 10, a first bearing seat 11 and a second bearing seat 12 that are mounted on the base 10, a lever core 13 inserted into the first bearing seat 11 and the second bearing seat 12, an operation lever 14 slidably arranged on the lever core 13, a touch switch 15 mounted on the operation lever 14, a master-end encoder 16 connected to the operation lever 14, and a null sensor 17 disposed between a head end and a tail end of the lever core 13. The null sensor 17 is disposed between the first bearing seat 11 and the second bearing seat 12. The operation lever 14 is capable of displacing (including rotary movement and axial movement) along an axis center on the lever core 13. The processor is communicably connected to the touch switch 15, the master-end encoder 16, and the null sensor 17. In the present disclosure, in the case that an operator controls the operation lever 14 to move forward or move backward on the lever core 13, the master-end encoder 16 records an operation lever displacement of the operation lever 14, and sends the operation lever displacement to the processor at intervals of a predetermined duration. The processor is equipped with a computer program to perform related steps to acquire target control information corresponding to the operation lever displacement generated by the operation lever 14 under a valid operation. In this way, the interventional robot slave end is accurately controlled based on the target control information, and errors are prevented. The predetermined duration is a predefined time length.

In this embodiment, the processor may be mounted on a master-end controller, or may be mounted on the interventional robot slave end, and may cause an elongated medical instrument (not illustrated) to accurately move, such that a better interventional surgical effect is ensured. As an example, the operator may singly control one operation lever to accurately control the interventional robot slave end to drive an elongated medical instrument (a catheter or a guide wire) to move, or non-simultaneously drive a plurality of elongated medical instruments (catheters or guide wires) to move. As another example, the master-end control apparatus includes at least two operation levers, and the operator may also control the two operation levers respectively using two hands. In this way, the operation levers are simultaneously or non-simultaneously controlled to move to accurately control the interventional robot slave end to drive the plurality of elongated medical instruments (the catheters or the guide wires) to move.

Generally, in the case that the current switch state is DISABLED, the operation lever 14 performs an invalid operation; in the case that the current sensor state is ENABLED, that is, the operation lever 14 is in a null region (the null region is a region, corresponding, the null sensor 17, on the lever core 13), the operation lever 14 performs an invalid operation; and in the case that the operation lever 14 moves to be in contact with the first bearing seat 11 and the second bearing seat 12 to cause the operation lever 14 to move backward and forward by a tiny distance, the operation lever 14 performs an invalid operation.

Figure 3:
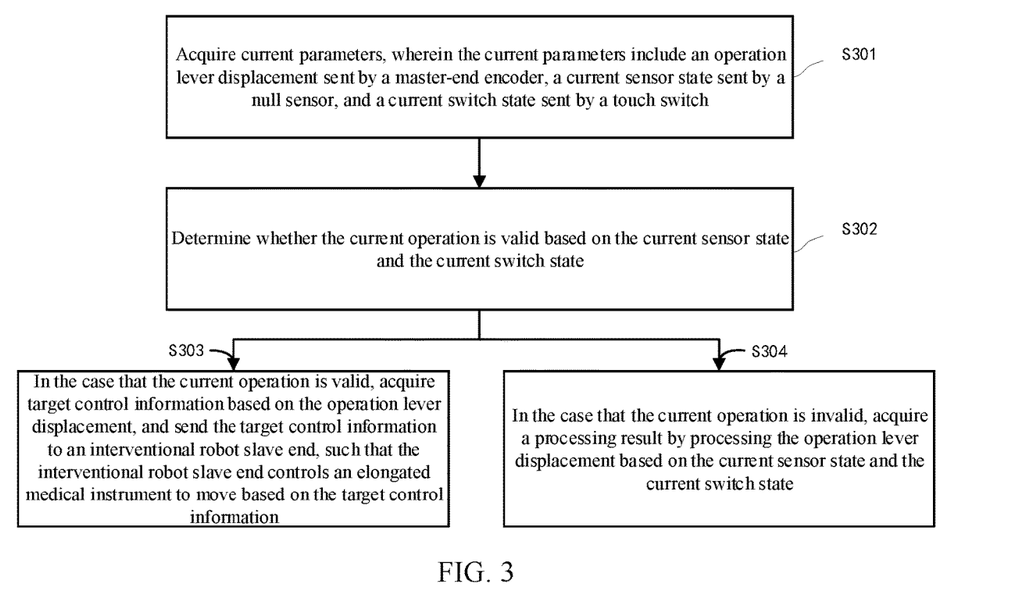
FIG. 3 is a schematic flowchart of a method for controlling an interventional robot according to some embodiments of the present disclosure.

To eliminate the invalid operation and ensure that the operator accurately controls the interventional robot slave end to drive a plurality of elongated medical instruments (catheters or guide wires) to move, as illustrated in FIG. 3, an embodiment of the present disclosure provides a method for controlling an interventional robot. The method is applicable to a processor, and includes the following steps.

In S301, current parameters are acquired, wherein the current parameters include an operation lever displacement sent by a master-end encoder, a current sensor state sent by a null sensor, and a current switch state sent by a touch switch.

The current parameters are parameters indicative of current states of devices connected to the processor. Specifically, the current states of the devices include the operation lever displacement of the operation lever on the lever core, the current sensor state, and the current switch state that are detected by the master-end encoder.

The operation lever displacement is a displacement generated at current time in response to the operation lever being operated by an operator. The operation lever displacement includes a current angular displacement (that is, a displacement generated in response to the operation lever 14 being controlled to rotate) and a current linear displacement (that is, a displacement generated in response to the operation lever 14 being controlled to linearly move).

The current sensor state is indicative of an operating state of the null sensor 17 at the current time. The current sensor state includes an ENABLED state and a DISABLED state. For example, the current sensor state $S1=1$ indicates that the null sensor 17 is enabled, and the current sensor state $S1=0$ indicates that the null sensor 17 is disabled. In this embodiment, in the case that the operation lever 14 is in the null region, corresponding to the null sensor 17, on the lever core 13, the current sensor state is ENABLED; and in the case that the operation lever 14 is not in the null region, corresponding to the null sensor 17, on the lever core 13, the current sensor state is DISABLED. The null region is a predetermined region, corresponding to the null sensor 17, on the lever core 13. A mounting direction of the null sensor 17 is parallel to a mounting direction of the lever core 13, a projection ray irradiates the null sensor 17 in a direction perpendicular to the mounting direction of the lever core 13, such that the null sensor 17 is projected on the lever core 13. In this case, a projection region is the null region, and the null region and the null sensor 17 have an equal length.

The current switch state is indicative of an operating state of the touch switch 15 at the current time. The current switch state includes an ENABLED state and a DISABLED state. For example, the current switch state $S2=1$ indicates that the touch switch 15 is enabled, and the current sensor state $S2=0$ indicates that the touch switch 15 is disabled. In the case that the operator holds the touch switch 15, the current state of the touch switch 15 is ENABLED; and in the case that the operator unholds the touch switch 15, the current state of the touch switch 15 is DISABLED.

In this embodiment, the master-end encoder 16 automatically sends the operation lever displacement to the processor, the null sensor 17 sends the current sensor state to the processor, and the touch switch 15 sends the current switch state to the processor. Afterwards, in the case that the operating states of the null sensor 17 and the touch switch 15 change, the null sensor 17 and the touch switch 15 automatically send the corresponding states thereof to the processor. In this way, the processor timely determines the operating state of the operation lever 14, and determines whether the current operation of the operation lever 14 is valid. The elongated medical instrument is controlled to perform the corresponding operation only in the case that the current operation is valid. This better assists the operator to accurately control the elongated medical instrument, such that a better surgical effect is achieved and the control accuracy is ensured.

In S302, whether the current operation is valid is determined based on the current sensor state and the current switch state.

The valid operation is an operation of the operation lever 14 capable of controlling the elongated medical instrument to move. It may be understood that the valid operation is an operation by which the operator desires to cause the elongated medical instrument to perform a corresponding action, for example, rotation (including forward rotation and reverse rotation), movement (including forward movement and backward movement), or the like. On the contrary, the invalid operation is an operation of the operation lever 14 incapable of controlling the elongated medical instrument to move, which may subject the elongated medical instrument to movement errors or useless efforts or the like. That is, the invalid operation is an operation by which the operator does not desire to cause the elongated medical instrument to perform the corresponding action.

In this embodiment, the processor determines whether the current operation of the operation lever 14 on the lever core 13 is valid, such that the control accuracy is ensured in performing different steps subsequently.

In S303, in the case that the current operation is valid, target control information is acquired based on the operation lever displacement, and the target control information is sent to an interventional robot slave end, such that the interventional robot slave end controls an elongated medical instrument to move based on the target control information.

In this embodiment, the operator holds and moves the touch switch 15 on the lever core 13, and the master-end encoder detects that the operation lever 14 moves on the lever core 13 and records the operation lever displacement thereof. At intervals of a predetermined duration, the master-end encoder sends the corresponding operation lever displacement to the processor. The processor acquires the target control information based on the operation lever displacement corresponding to the valid operation, and sends the target control information to the interventional robot slave end, such that the interventional robot slave end controls the elongated medical instrument to move based on the target control information. In this way, the surgical effect desired by the operator is achieved, movement of the elongated medical instrument is accurately controlled, the control method is flexible, and operation needs of different operators are accommodated.

Further, in the case that a plurality of elongated medical instruments are employed, the master-end control apparatus further includes an instrument change switch connected to the processor. In step S301, the current parameters further include a target drive identifier. Step S303, that is, sending the target control information the interventional robot slave end such that the interventional robot slave end controls the elongated medical instrument to move based on the target control information, includes: sending the target drive identifier and the target control information to the interventional robot slave end, such that the interventional robot slave end controls the elongated medical instrument corresponding to the target drive identifier to move based on the target control information.

The target drive identifier is a unique identifier by which the elongated medical instrument is identifiable by the interventional robot slave end. In this embodiment, the interventional robot slave end is capable of clamping a plurality of catheters or guide wires. In the case that the interventional robot slave end acquires the target drive identifier, the catheter or the guide wire that needs to be driven by the operator may be determined, and thus the elongated medical instrument may be accurately controlled. Exemplarily, the conventional elongated medical instrument of the interventional robot slave end includes a support catheter M1, a middle catheter M2, and a guide wire M3. In the case that the target drive identifier is M2, the middle catheter needs to be driven.

In this embodiment, the operator operates the instrument change switch to select the elongated medical instrument to be operated to generates the target drive identifier, and send the target drive identifier to the processor. The processor sends the target drive identifier and the target control information to the interventional robot slave end, such that the interventional robot slave end controls the elongated medical instrument corresponding to the target drive identifier to move based on the target control information, such that the actual surgical needs of the operator are accommodated.

In S304, in the case that the current operation is invalid, a processing result is acquired by processing the operation lever displacement based on the current sensor state and the current switch state.

In this embodiment, in the case that the current operation of the operation lever 14 on the lever core 13 is invalid, the processor controls a corresponding master-end device to perform a specific operation to cancel the invalid operation of the operation lever 14 on the lever core 13, instead of controlling the elongated medical instrument corresponding to the target drive identifier. In this way, the operation lever displacement generated by the invalid operation is eliminated, the surgical effect desired by the operator is achieved, and the interventional surgery is ensured successful.

In the method for controlling the interventional robot according to this embodiment, the processor determines, based on the current sensor state and the current switch state, whether the current operation of the operation lever 14 on the lever core 13 is valid. In this way, the processor timely determines the operating state of the operation lever 14, and controls the elongated medical instrument to perform the corresponding operation only in the case that the current operation of the operation lever 14 is valid, such that the control accuracy is ensured. In the case that the current operation of the operation lever 14 on the lever core 13 is valid, the target control information is acquired based on the operation lever displacement, and the target driver identifier and the target control information are sent to the interventional robot slave end, such that the interventional robot slave end controls the elongated medical instrument corresponding to the target drive identifier to move based on the target control information. In this way, the elongated medical instrument is flexibly controlled to move, and operation needs of different operators are accommodated. In the case that the current operation of the operation lever 14 on the lever core 13 is invalid, the processing result is acquired by processing the operation lever displacement based on the current sensor state and the current switch state. In this way, the invalid operation is canceled, the surgical effect desired by the operator is achieved, and the interventional surgery is ensured successful.

Figure 4:
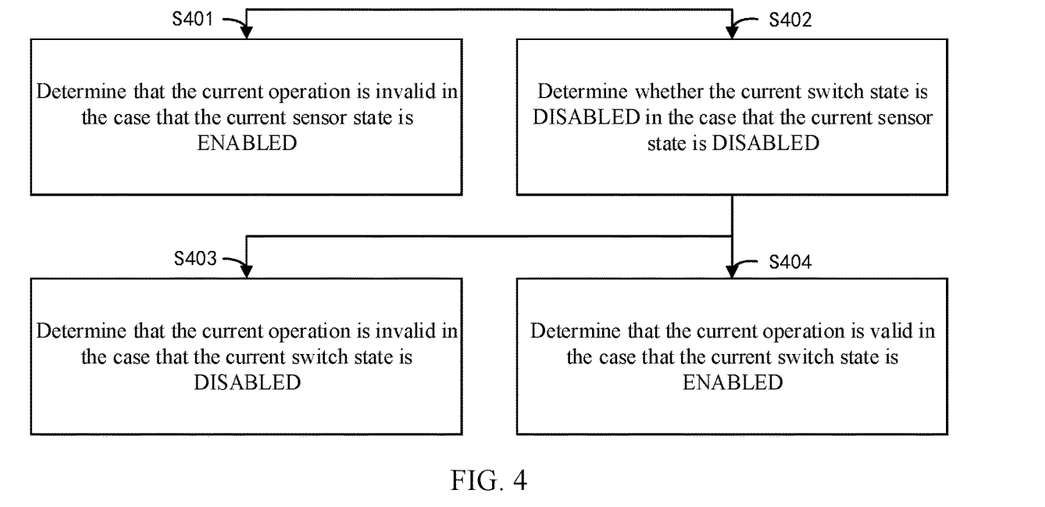
FIG. 4 is a schematic flowchart of step 5302 in FIG. 3.

In an embodiment, as illustrated in FIG. 4, step S302, that is, determining, based on the current sensor state and the current switch state, whether the current operation is valid, includes the following steps.

In S401, it is determined that the current operation is invalid in the case that the current sensor state is ENABLED.

In this embodiment, the null region is also referred to as a reset region. That is, in the case that the operator unholds the touch switch and the operation lever 14 is outside the null region, the operation lever 14 may be brought by the motor back to the null region. In the case that the operation lever 14 moves to the null region, the current sensor state corresponding to the null sensor 17 changes from DISABLED to ENABLED, and the motor stops operating. As a result, the position at which the operation lever 14 stops in the null region is random and not unique, such that the displacements by which the operation lever 14 is movable on the lever core 13 at different times are different. However, the operator fails to observe such differences, which is unfavorable to carrying out the surgery. In this way, the elongated medical instrument fails to be accurately controlled. For example, the displacement by which the operation lever 14 is movable on the lever core 13 at the first time is +xx mm, and the displacement by which the operation lever 14 is movable on the lever core 13 at the second time is +yy mm.

In this embodiment, in the case that the current sensor state is ENABLED, the current operation of the operation lever 14 on the lever core 13 is determined invalid, that is, the operation lever 14 is in the null region. In this case, no matter whether the operator operates the operation lever 14, the current operation of the operation lever 14 on the lever core 13 is constantly invalid. That is, the operation is valid only in the case that the operation lever is outside the null region and the current sensor state is DISABLED, such that it is ensured that the displacement by which the operation lever 14 moves on the lever core 13 is fixed each time. In this way, the elongated medical instrument is accurately controlled, the invalid operation is canceled, and the errors are prevented.

In S402, whether the current switch state is DISABLED is determined in the case that the current sensor state is DISABLED.

In this embodiment, upon power on, the touch switch 15 automatically sends the current switch state to the processor; and in the case that the current switch state of the touch switch 15 changes, the current switch state is also automatically sent to the processor, such that the processor timely determines the current switch state of the touch switch 15.

In S403, it is determined that the current operation is invalid in the case that the current switch state is DISABLED.

In this embodiment, in the case that the current sensor state is DISABLED, it indicates that the operation lever 14 is outside the null region; and in the case that the current switch state of the touch switch 15 is DISABLED, it indicates that the operator unholds the touch switch 15. In this case, where the current operation of the operation lever 14 is present on the lever core 13, the motor brings the operation lever 14 back to the null region, and the current operation is invalid.

In S404, it is determined that the current operation is valid in the case that the current switch state is ENABLED.

In this embodiment, in the case that the current sensor state is DISABLED and the current switch state is ENABLED, the operation lever is outside the null region and the operator holds the touch switch. In this case, the current operation of the operation lever on the lever core is valid, and subsequently the elongated medical instrument is controlled for the interventional robot slave end based on the operation lever displacement of the operation lever on the lever core.

In an embodiment, in the case that the current sensor state is ENABLED, step S304, that is, acquiring the processing result by processing the operation lever displacement based on the current sensor state and the current switch state in the case that the current operation of the operation lever 14 is considered invalid, includes:

determining the operation lever displacement corresponding to the current operation as 0 in the case that the current switch state is ENABLED.

In this embodiment, in the case that the current sensor state is ENABLED, the operation lever 14 is in the null region on the lever core 13. In this case, no matter whether the current switch state is ENABLED, the current operation of the operation lever 14 on the lever core 13 is constantly invalid. In the case that the current sensor state is ENABLED and the current switch state is ENABLED, it indicates that the operator holds the touch switch 15, such that the operation lever 14 performs an operation on the lever core 13; or in the case that the current switch state is DISABLED, the operator unholds the operation lever 14.

In this embodiment, in the case that the current sensor state is ENABLED, the current operation of the operation lever 14 on the lever core 13 is invalid, such that it is ensured that the length of the displacement of the operation lever 14 is movable on the lever core 13 is fixed. In this way, the accuracy of the surgery carried out by the operator is ensured, and the errors that fail to be observed by human eyes are prevented.

In an embodiment, the master-end control apparatus further includes a motor connected to the processor. In the case that the current sensor state is DISABLED and the current switch state is DISABLED, S304, that is, acquiring the processing result by processing the operation lever displacement based on the current sensor state and the current switch state in the case that the current operation is invalid, includes: sending a motor start signal to the motor, such that the motor controls the operation lever to perform a reset operation and reset the operation lever displacement of the operation lever.

The motor start signal is a signal configured to control start of the motor to cause the operation lever 14 to reset.

Generally, upon completion of the surgery by the operator, the operation unholds the operation lever 14, and the processor sends the motor start signal to the motor, such that the motor performs the reset operation to drive the operation lever 14 to move to the null region. In this case, the surgery ends. Specifically, controlling, by the motor, the operation lever to reset includes: controlling, by the motor, the operation lever to move towards the null sensor. In the case that the operation lever moves to the null region of the null sensor, the current sensor state corresponding to the null sensor is changed to ENABLED. The null sensor sends a sensor signal including the ENABLED state to the motor, such that the motor controls the operation lever to stop at the null region corresponding to the null sensor.

Specifically, the processor sends the motor start signal carrying a reset direction to the motor, such that the motor drives, based on the reset direction, the operation lever 14 to move towards the null sensor 17. In the case that the operation lever 14 moves to the null region corresponding to the null sensor 17, the null sensor 17 detects the operation lever 14, automatically changes the current sensor state from DISABLED to ENABLED, and sends the current sensor state as ENABLED to the motor, such that the motor stops operating. The reset direction refers to a direction in which the motor moves towards the null sensor 17.

Figure 5:
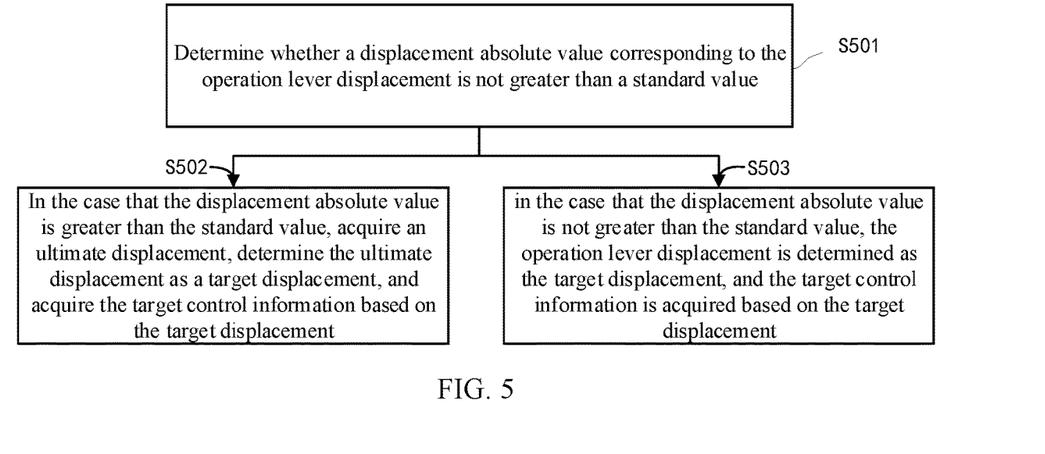
FIG. 5 is a schematic flowchart of step 5303 in FIG. 3.

In an embodiment, as illustrated in FIG. 5, in the case that the current sensor state is DISABLED and the current switch state is ENABLED, S303, that is, acquiring the target control information based on the operation lever displacement in the case that the current operation is valid, includes the following steps.

In S501, whether a displacement absolute value corresponding to the operation lever displacement is not greater than a standard value is determined.

The displacement absolute value is an absolute value of the operation lever displacement. The standard value is a predetermined value, which is specifically a maximum distance by which the operation lever 14 is movable. The standard value is less than a distance from the null sensor 17 to the first bearing seat 11 or a distance from the null sensor 17 to the second bearing seat 12.

Generally, the null sensor 17 is arranged on the base 10, and is disposed at a position corresponding to the middle of the lever core 13. In the case that the operation lever 14 moves towards the first bearing seat 11, the interventional robot slave end drives the elongated medical instrument to move forward; and in the case that the operation lever 14 moves away from the first bearing seat 11, the interventional robot slave end drives the elongated medical instrument to move backward. However, in the case that the operation lever 14 is in contact with the first bearing seat 11 or the second bearing seat 12, due to inertia, the operation lever 14 reciprocates within a small range, and the interventional robot slave end may drive the elongated medical instrument to generate a back-forth movement that is not easily noticeable by human eyes or a movement speed of the elongated medical instrument may abruptly change. In this case, where a displacement generated by the back-forth movement or the movement speed of the abrupt change is sent to the interventional robot slave end, the interventional robot slave end does useless efforts, and the control effect desired by the operator fails to be achieved. In addition, the back-forth movement or the abrupt change of the movement speed of the elongated medical instrument exerts some adverse effects.

In this embodiment, in the case that the current sensor state is DISABLED, the current switch state is ENABLED, this indicates that the operation lever is outside the null region and the operation lever is held by the operator. In this case, the current operation of the operation lever on the lever core is valid. The displacement absolute value is compared with the standard value to determine whether the operation lever displacement is less than the standard value, such that a corresponding operation is performed subsequently.

In S502, in the case that the displacement absolute value is greater than the standard value, an ultimate displacement is acquired, the ultimate displacement is determined as a target displacement, and the target control information is acquired based on the target displacement.

The ultimate displacement is a displacement corresponding to the standard value. The target displacement is a displacement to determine the target control information.

Specifically, in the case that the displacement absolute value is greater than the standard value, it indicates that the operation lever displacement exceeds the ultimate displacement corresponding to the standard value, and the operation lever 14 may be in contact with the first bearing seat 11 or the second bearing seat 12. Therefore, the operation lever displacement exceeding the standard value needs to be processed. In this embodiment, in the case that the displacement absolute value is greater than the standard value, the ultimate displacement corresponding to the standard value is determined as the target displacement. The target control information is acquired based on the target displacement to eliminate the adverse effects exerted by the back-forth movement or the abrupt change of the movement speed of the elongated medical instrument due to the operation lever displacement exceeding the standard value.

In S503, in the case that the displacement absolute value is not greater than the standard value, the operation lever displacement is determined as the target displacement, and the target control information is acquired based on the target displacement.

In this embodiment, in the case that the displacement absolute value is not greater than the standard value, it indicates that the operation lever displacement does not exceed the ultimate displacement corresponding to the standard value, and it is impossible that the operation lever 14 is contact with the first bearing seat 11 or the second bearing seat 12. Therefore, the target control information needs to be acquired based on the operation lever displacement to accurately control the elongated medical instrument.

Figure 6:
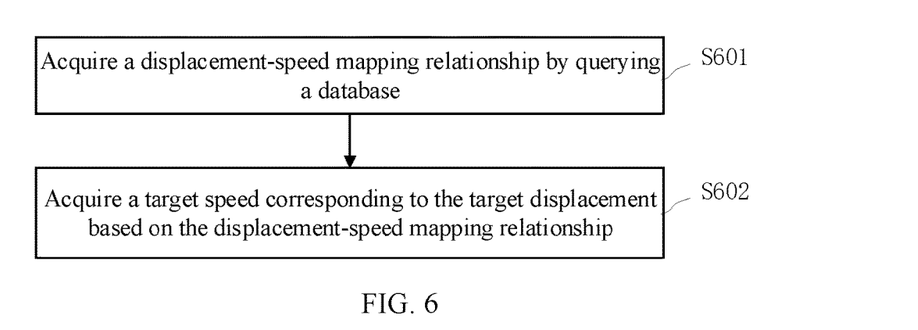
FIG. 6 is a schematic flowchart of step 5502 or 5503 according to some embodiments of the present disclosure.

In an embodiment, as illustrated in FIG. 6, S502 or S503, that is, acquiring the target control information based on the target displacement, includes the following steps.

In S601, a displacement-speed mapping relationship is acquired by querying a database.

A displacement-speed table is a table prestored in the database and recording displacement-speed mapping relationships.

In S602, a target speed corresponding to the target displacement is acquired based on the displacement-speed mapping relationship.

In this embodiment, in the case that the current operation of the operation lever on the lever core is valid, the displacement-speed table is queried to acquire the displacement-speed mapping relationship, and the target displacement is introduced into the displacement-speed mapping relationship to acquire the target control information, such that the interventional robot slave end drives, based on the target control information, the elongated medical instrument corresponding to the target drive identifier, and thus the elongated medical instrument is accurately controlled. The operation is simple and efficient, and the needs of different operation speeds of the operator are accommodated. In addition, the length of the lever core is limited, and thus to control the elongated medical instrument to reach a position desired by the operator, the operator needs to cause the operation lever 14 to reset for multiple times. Therefore, due to the time for resetting the operation lever, the time for the surgery is increased. In this embodiment, based on the target displacement generated in response to the movement of the operation lever 14, the movement speed of the elongated medical instrument is controlled. In this way, in one vascular interventional surgery, the elongated medical instrument is ensured to continuously move, with no need of waiting until the operation lever stops resetting, and movement continuity of the elongated medical instrument is ensured. In this way, the processor does not need to perform complicated calculations, and resetting of the operation lever is reduced to shorten the time for the surgery.

Figure 7:
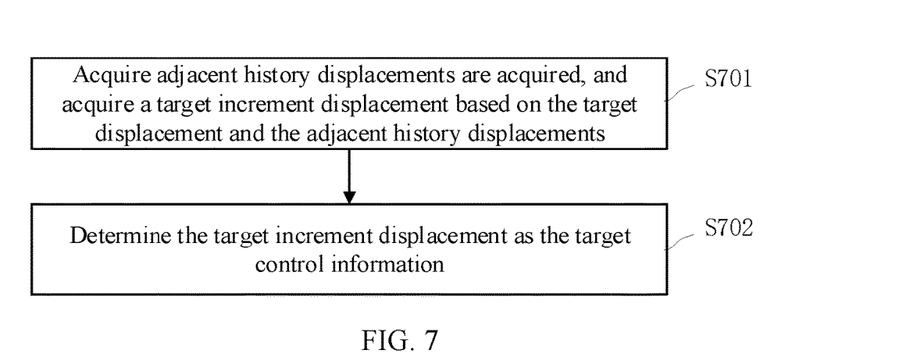
FIG. 7 is a schematic flowchart of step 5502 or 5503 according to some embodiments of the present disclosure.

In an embodiment, as illustrated in FIG. 7, S502 or S503, that is, acquiring the target control information based on the target displacement, includes the following steps.

In S701, adjacent history displacements are acquired, and a target increment displacement is acquired based on the target displacement and the adjacent history displacements.

In S702, the target increment displacement is determined as the target control information.

The operation lever displacement is a displacement of the operation lever 14 at current time, and may be understood as a real-time displacement. The adjacent history displacement is a displacement of the operation lever 14 prior to a predetermined duration ahead of the current time.

In this embodiment, the master-end encoder 16 sends the target displacement to the processor, and the processor acquires the adjacent history displacements by querying the database, such that the target increment displacement is acquired based on the target displacement and the adjacent history displacements, and the target increment displacement is determined as the target control information. The interventional robot slave end may drive the elongated medical instrument corresponding to the target drive identifier to move by the target increment displacement, such that the elongated medical instrument is accurately controlled. Exemplarily, a predetermined time interval is 30 ms, the displacement corresponding to 30 ms is 100 mm; the displacement corresponding to 60 ms is 220 mm, and in this case, 220 mm is equal to the displacement 100 mm generated within 0 to 30 ms plus the displacement 120 mm generated within 30 to 60 ms; and the displacement corresponding to 90 ms is 290 mm, and in this case, 209 mm is equal to the displacement 100 mm generated within 0 to 30 ms, plus the displacement 120 mm generated within 30 to 60 ms, and plus the displacement 70 ms generated within 30 to 60 ms. In the case the displacement is 290 mm corresponding to 90 ms at current time and the adjacent history displacement is 220 mm corresponding to 60 ms, the target increment displacement is 70 mm. It may be understood that the interventional robot slave end may process the target increment displacement by a linear mapping relationship, scaling up, scaling down, or other mapping relationships, and thus acquire displacement data for controlling the elongated medical instrument.

In the method for controlling the interventional robot according to the present disclosure, the processor controls, based on the current sensor state and the current switch state, the elongated medical instrument to move based on the target control information only in the case that the current operation of the operation lever 14 is valid. In this way, the elongated medical instrument is flexibly controlled to move, and operation needs of different operators and the needs of different operation speeds are accommodated.

An embodiment of the present disclosure further provides a readable storage medium. The readable storage medium stores thereon one or more computer programs. The one or more computer programs, when loaded and run by a processor, cause the processor to perform the steps of the method for controlling the interventional robot according to the above embodiments, for example, S301 to S304 as illustrated in FIG. 3, or the steps illustrated in FIG. 4 to FIG. 7, which are not described herein any further for brevity.

Persons of ordinary skill in the art may understand that all or part of the steps of the methods in the embodiments may be implemented by a program instructing relevant hardware. The computer program may be stored in a non-volatile computer-readable storage medium. When the computer program runs, the steps of the methods in the embodiments are performed. References to the memory, the storage, the database, or other media used in the embodiments of the present disclosure may all include a non-volatile and/or or a volatile memory. The non-volatile memory may include a read-only memory (ROM), a programmable ROM (PROM), an electrically programmable ROM (EPROM), an electrically erasable programmable ROM (EEPROM), or a flash memory. The volatile memory may include a random-access memory (RAM) and a high-speed cache or the like. By way of illustration rather than limitation, the RAM may be obtained in a plurality of forms, such as a static RAM (SRAM), a dynamic RAM (DRAM), a synchronous DRAM (SDRAM), a double data rate SDRAM (DDRSDRAM), an enhanced SDRAM (ESDRAM), a synchlink DRAM (SLDRAM), a rambus direct RAM (RDRAM), a direct rambus dynamic RAM (DRDRAM), and a rambus dynamic RAM (RDRAM).

A person skilled in the art may clearly understand that, for the purpose of convenient and brief description, the division of functional unit or modules is merely used as example for description, and in practical application, the functions may be allocated to and completed by different functional units or modules as required, that is, an internal structure of the apparatus is divided into different functional units or modules, to complete all or some of functions described above.

In summary, it should be finally noted that the above-described embodiments are merely for illustration of the technical solutions of the present disclosure, but are not intended to limit the present disclosure. Although the present disclosure is described in detail with reference to these embodiments, a person skilled in the art may also make various modifications to the technical solutions disclosed in the embodiments, or make equivalent replacements to a part of the technical features contained therein. Such modifications or replacements, made without departing from the principles of the present disclosure, shall fall within the scope of the present disclosure.

Described above are merely several exemplary embodiments for illustration of the present disclosure, which are specifically described in detail. However, these embodiments shall not be construed as limitations to the scope of the present disclosure. It should be noted that persons of ordinary skill in the art may derive various variations and modifications without departing from the inventive concept of the present disclosure. Such variations and modifications shall pertain to the protection scope of the present disclosure. Therefore, the protection scope of the present disclosure is subject to what defined by the appended claims.

What is claimed is:

1. An interventional robot system, comprising a processor, a master-end control apparatus, and an interventional robot slave end, wherein the master-end control apparatus comprises a base, an operation lever, a touch switch, a master-end encoder, and a null sensor; wherein
   the touch switch is arranged on the operation lever and connected to the processor, and is configured to send a current switch state to the processor;
   the master-end encoder is arranged on the operation lever and connected to the processor, and is configured to send to the processor an operation lever displacement generated in response to the operation lever being controlled to perform a current operation;
   the null sensor is arranged on the base and connected to the processor, and is configured to send a current sensor state to the processor; and
   the processor is configured to: acquire the operation lever displacement sent by the master-end encoder, the current sensor state sent by the null sensor, and the current switch state sent by the touch switch; determine, based on the current sensor state and the current switch state, whether the current operation is valid; in response to determining that the current operation is valid, acquire target control information based on the operation lever displacement and send the target control information to the interventional robot slave end, such that the interventional robot slave end controls an elongated medical instrument to move based on the target control information; and in response to determining that the current operation is invalid, acquire a processing result by processing the operation lever displacement based on the current sensor state and the current switch state.

2. The interventional robot system according to claim 1, wherein the null sensor is arranged on the base, and is disposed between a head end of the operation lever and a tail end of the operation lever.

3. A readable storage medium, storing one or more computer programs, wherein the one or more computer programs, when loaded and run by a processor, cause the processor to perform a method for controlling an interventional robot comprising:
- (1) acquiring current parameters, the current parameters comprising an operation lever displacement sent by a master-end encoder, a current sensor state sent by a null sensor, and a current switch state sent by a touch switch, wherein the operation lever displacement is a displacement generated in response to the operation lever being controlled to perform a current operation;
- (2) determining, based on the current sensor state and the current switch state, whether the current operation is valid;
- (3) in response to determining that the current operation is valid, acquiring target control information based on the operation lever displacement and sending the target control information to an interventional robot slave end, such that the interventional robot slave end controls an elongated medical instrument to move based on the target control information;
- (4) in response to determining that the current operation is invalid, acquiring a processing result by processing the operation lever displacement based on the current sensor state and the current switch state.

4. The readable storage medium according to claim 3, step (2) comprises:
- determining that the current operation is invalid in the case that the current sensor state is ENABLED;
- determining whether the current switch state is DISABLED in the case that the current sensor state is DISABLED;
- determining that the current operation is invalid in the case that the current switch state is DISABLED; and
- determining that the current operation is valid in the case that the current switch state is ENABLED.

5. The readable storage medium according to claim 4, wherein in the case that the current sensor state is ENABLED and the current operation is invalid, acquiring the processing result by processing the operation lever displacement based on the current sensor state and the current switch state comprises:
- determining the operation lever displacement corresponding to the current operation as 0 in the case that the current switch state is ENABLED.

6. The readable storage medium according to claim 5, wherein the master-end control apparatus further comprises a motor connected to the processor; and
- in the case that the current sensor state is DISABLED, the current switch state is DISABLED, and the current operation is invalid, acquiring the processing result by processing the operation lever displacement based on the current sensor state and the current switch state comprises:
  sending a motor start signal to the motor, such that the motor controls the operation lever to perform a reset operation and resets the operation lever displacement.

7. The readable storage medium according to claim 4, wherein in the case that the current sensor state is DISABLED, the current switch state is ENABLED, and the current operation is valid:
- acquiring the target control information based on the operation lever displacement comprises:
- determining whether a displacement absolute value corresponding to the operation lever displacement is not greater than a standard value;
- in response to determining that the displacement absolute value is greater than the standard value, acquiring an ultimate displacement, determining the ultimate displacement as a target displacement, and acquiring the target control information based on the target displacement; or
- in response to determining that the displacement absolute value is not greater than the standard value, determining the operation lever displacement as a target displacement, and acquiring the target control information based on the target displacement.

8. The readable storage medium according to claim 7, wherein acquiring the target control information based on the target displacement comprises:
- acquiring a displacement-speed mapping relationship by querying a database; and
- acquiring, based on the displacement-speed mapping relationship, a target speed corresponding to the target displacement, and determining the target speed as the target control information.

9. The readable storage medium according to claim 7, wherein acquiring the target control information based on the target displacement comprises:
- acquiring adjacent history displacements, and a target increment displacement based on the target displacement and the adjacent history displacements; and
- determining the target increment displacement as the target control information.

10. The readable storage medium according to claim 3, wherein the master-end control apparatus further comprises an instrument change switch connected to the processor, and the current parameters further comprise a target drive identifier sent by the instrument change switch; and
- in step (3), the target drive identifier and the target control information are sent to the interventional robot slave end, such that the interventional robot slave end controls the elongated medical instrument corresponding to the target drive identifier to move based on the target control information.

* * * * *